US00PP36980P2

(12) United States Plant Patent
Chaussard

(10) Patent No.: US PP36,980 P2
(45) Date of Patent: Sep. 23, 2025

(54) ***HIBISCUS* PLANT NAMED 'Minsycbb2b'**

(50) Latin Name: *Hibiscus syriacus*
Varietal Denomination: Minsycbb2b

(71) Applicant: Hortival Diffusion SAS, Beaufort en Anjou (FR)

(72) Inventor: Pierre Chaussard, Saint-Mathurin-sur-Loire (FR)

(73) Assignee: HORTIVAL DIFFUSION SAS, Beaufort en Anjou (FR)

( * ) Notice: Subject to any disclaimer, the term of this patent is extended or adjusted under 35 U.S.C. 154(b) by 0 days.

(21) Appl. No.: 19/004,919

(22) Filed: Dec. 30, 2024

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
CPC ..... A01H 6/608; A01H 5/02
See application file for complete search history.

(56) References Cited

U.S. PATENT DOCUMENTS

PP20,574 P2 12/2009 Woods

OTHER PUBLICATIONS

Minier Professional Solutions Catalogue, 2024-2025 (Oct. 2024), obtained from https://www.pepinieres-minier.fr/Catalogue%202425_BD.pdf.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of hibiscus plant, referred to by its cultivar name, 'Minsycbb2b', is disclosed. The new variety displays white and light blue-colored inflorescences. Medium-green colored foliage is formed. The growth habit is tall and semi-upright. Additionally, the new variety is particularly well suited for growing as distinctive ornamentation in the landscape.

2 Drawing Sheets

Latin name of genus and species of plant claimed: *Hibiscus syriacus.*

Variety denomination: 'Minsycbb2b'.

STATEMENT REGARDING PRIOR DISCLOSURES BY THE INVENTOR

The first offer for sale of the new variety was October 2024, in the publication of Pepinieres Minier Professional Solutions Catalogue 2024-2025. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Hibiscus syriacus* plant originated in a controlled breeding program in La Menitre, France in August 2016. The objective of the breeding program was to develop new Hibiscus cultivars with blue flowers. The new cultivar is the result of cross pollination wherein two parents were crossed which previously had been studied in the hope that they would contribute the desired characteristics. The female parent (i.e., the seed parent) of the new cultivar is a proprietary breeding selection (not patented). The male parent (i.e., the pollen parent) of the new cultivar is *Hibiscus syriacus* 'Notwood3' (U.S. Plant Pat. No. 20,574).

The parentage of the new variety can be summarized as follows: proprietary breeding selection x 'Notwood3'

The seeds resulting from the above cross pollination were sown and small plants were obtained which were physically and biologically different from each other. The new cultivar was selected as a single flowering plant during September 2019, in a controlled environment in La Menitre, France.

The new variety has been found to undergo asexual propagation by grafting in La Menitre, France. Asexual propagation by grafting in La Menitre, France has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of hibiscus plant of the present invention possesses the following combination of characteristics:

(a) forms white and light blue-colored inflorescences,
(b) displays medium green-colored foliage, and
(c) exhibits a tall, semi-upright growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the new variety displays blue sectors flowers compared to the pink sectors of the proprietary breeding selection (i.e., the seed parent). Additionally, the new variety forms flowers that are mostly white with only sectors of blue coloring compared to the flowers of the 'Notwood3' variety (i.e., the pollen parent), whose whole flowers are blue. Moreover, the new variety can be readily distinguished from non-parental related similar varieties. For example, the new variety forms flowers that are white with blue sectors and a pink basal spot, compared to the 'Minspot' variety (not patented) which forms flowers that are white with pink sectors and a red basal spot and produce fewer petaloids than the new variety.

The new variety has been named 'Minsycbb2b'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Minsycbb2b' variety. The photographed plants were approximately two years old and grown in a field in La Menitre, France in September 2023.

DETAILED BOTANICAL DESCRIPTION

Figure 1:
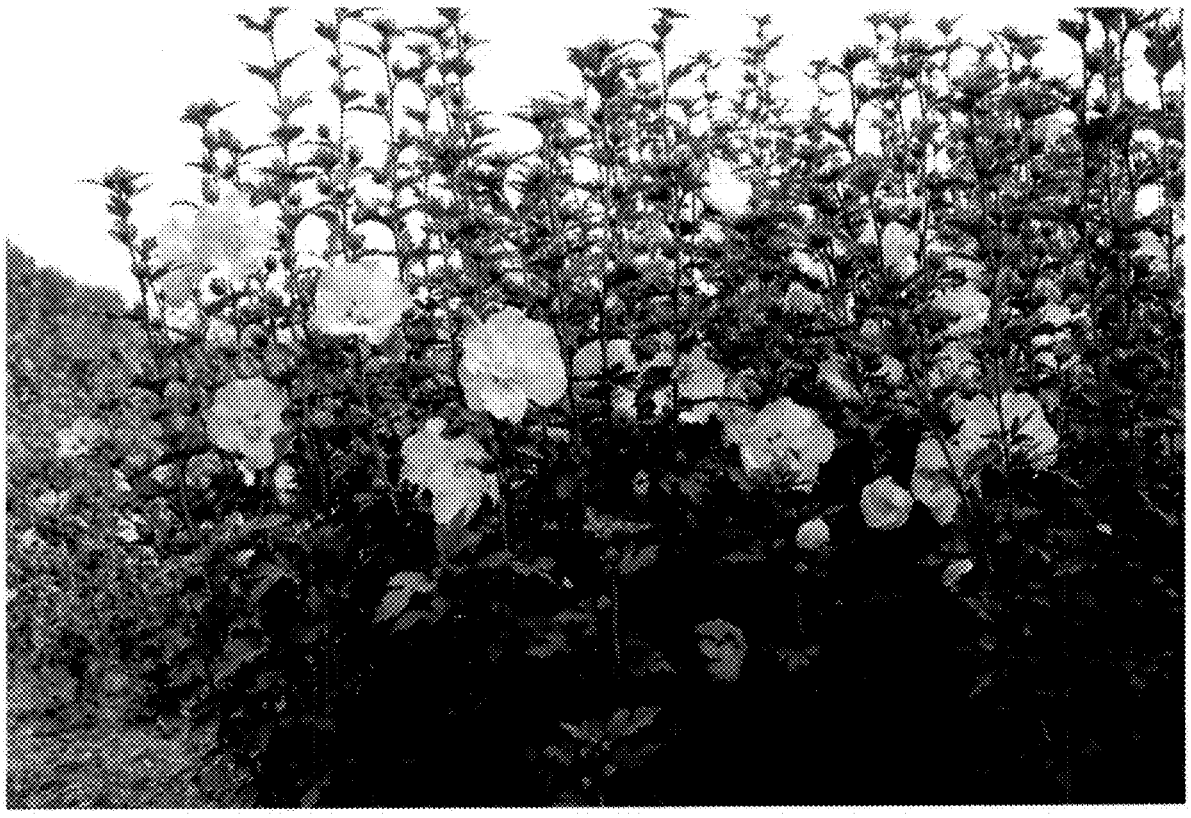
FIG.1 illustrates a specimen of the plant, displaying the overall growth and flowering habit-side view.
Figure 2:
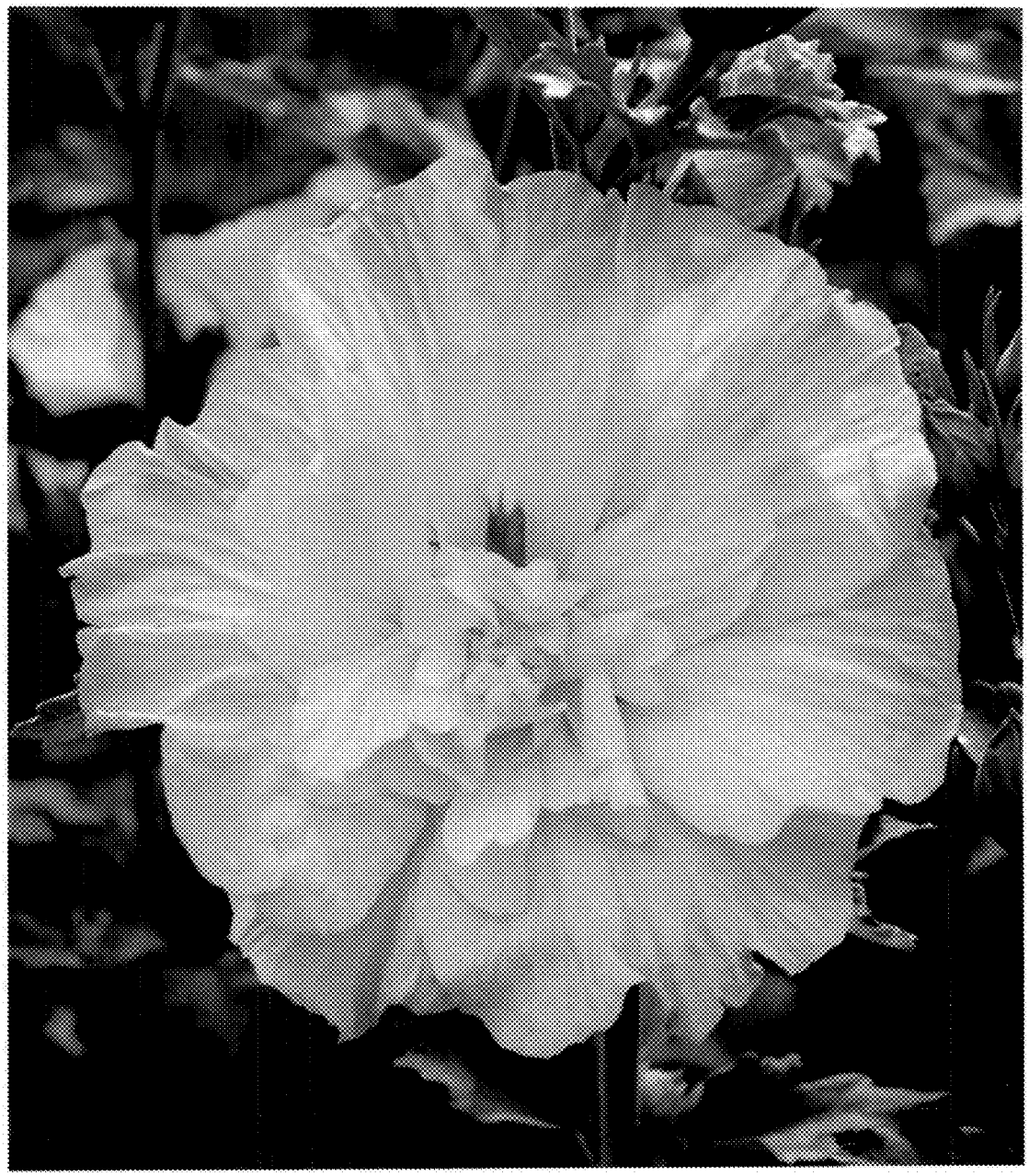
FIG. 2 illustrates a specimen of an inflorescence from a plant of the new variety-close-up view.

The chart used in the identification of the colors is that of the Royal Horticultural Society (R.H.S. Colour Chart), 2015 edition, London, England. The terminology which precedes reference to the chart has been added to indicate the corresponding color in more common terms and The R.H.S. Colour Chart designation used herein represents the closest color observed on the majority of the specified botanical feature. The color values were determined in September 2024, under natural light conditions in Cochranville, Pennsylvania. The description is based on the observation of plants produced from cuttings from stock plants and grown in two-gallon containers for approximately 18 months in a greenhouse in Cochranville, Pennsylvania.

Botanical classification: *Hibiscus syriacus* cultivar 'Minsycbb2b'.

PROPAGATION:

*Type cutting*.—Softwood cuttings.

*Time to initiate roots during the summer*.—Approximately 40 days on average.

*Time to produce a rooted young plant, summer*.—Approximately 5 months on average.

*Root description*.—White, medium thickness, fibrous.

*Rooting habit*.—Moderate branching and density.

Plant:

*Habit*.—Deciduous shrub, semi-upright habit.

*Commercial crop time*.—Approximately 28 months from a rooted cutting to finish in a 1-gallon container on average.

*Hardiness*.—USDA Zones 5-9.

*Size*.—Approximately 70.0 cm in height from soil level to top of plant plane on average; and approximately 27.0 cm in width on average.

Branches:

*Branching habit*.—Freely branching, pinching enhances branching.

*Auantity of lateral branches per plant*.—Approximately 8 on average.

*Shape*.—Round.

*Strength*.—Strong.

*Size*.—length: Approximately 22.0 cm on average. diameter: Approximately 4.0 mm on average. length of central internode: approximately 3.4 cm on average.

*Texture*.—Young stems: minutely pubescent and pulverulent. mature stems: glabrate.

*Color young stems*.—Grey-Brown Group 199D. mature stems: Brown Group 200C.

Foliage:

*Number of leaves*.—Approximately 28 per lateral branch on average.

*Fragrance*.—None detected.

*Form*.—Simple.

*Arrangement*.—Alternate, with some nodes having multiple leaves.

Leaves:

*Aspect*.—Flat.

*Shape general*.—Overall rhomboid to ovate, with three deep lobes. margin: lobed. apex: acute. base: attenuate.

*Venation*.—Palmate.

*Size*.—Length of mature leaf: approximately 8.0 cm on average. width of mature leaf: approximately 4.5 cm on average.

*Texture*.—upper surface: slightly rough. lower surface: rough, with distinct veins.

*Color*.—Upper surface of young foliage: Green Group 139A, with venation of Yellow-Green Group 147D. lower surface of young foliage: Green Group 137C with venation Yellow-Green Group 147D. upper surface of mature foliage: Green Group 137B with venation of Yellow-Green Group 147C. lower surface of mature foliage: Yellow-Green Group 146B with venation of Yellow-Green Group 147D.

*Petiole*.—Length: approximately 1.5 cm on average. width: approximately 1.2 mm on average. texture of upper and lower surfaces: pubescent. color of upper and lower surfaces: Green Group 137C.

Inflorescence:

*Type*.—Single, axillary.

*Shape*.—Rotate, 5 petals arranged in a single whorl.

*Depth*.—Approximately 3.0 cm on average.

*Width*.—Approximately 7.0 cm on average.

*Habit*.—Whorl.

*Persistent or self-cleaning*.—Self-cleaning.

*Lastingness of individual flower*.—Typically 2 to 3 days.

*Fragrance*.—Absent.

*Bud*.—shape: Round to oval. length: Approximately 2.0 cm on average. diameter: approximately 1.5 cm on average. color: Yellow-Green Group 147C.

*Petals*.—Quantity: 5. shape: obovate to obdeltoid. appearance: delicate with slightly undulate edges. arrangement: whorled, moderately overlapping. attitude of outermost petal: moderately ascending. margin: undulate. apex: obtuse. base: acute. length: approximately 4.7 cm on average. width: approximately 4.0 cm on average. texture of upper and lower surfaces: glabrous. color of upper and lower surfaces when opening: White Group NN155C. color of upper and lower surfaces when fully opened: White Group NN155C, with outer edges of Violet-Blue Group 92D. petal eye color, upper surface: Red-Purple Group 61B. petal eye color, lower surface: Red-Purple Group 64D. petal eye size: small.

*Petaloids*.—Quantity: typically 15 to 25. arrangement: whorled. length: typically 1.5 cm to 3.3 cm. width: typically 0.6 cm to 1.2 cm. shape: spatulate, variable. margin: entire, undulate. color, upper and lower surfaces: White Group NN155C.

*Calyx*.—Shape: funnelform. length: approximately 1.8 cm on average. diameter. approximately 2.4 cm on average. sepals quantity per flower: 5. length: approximately 18.0 mm on average. width: approximately 8.0 mm on average. shape: deltoid. apex: acute. base: fused. margin: entire. texture, upper surface: slightly farinose. texture, lower surface: glabrous. color, upper surface: Yellow-Green Group 147B. color, lower surface: Green Group 139C.

*Peduncles*.—Strength: strong. angle: approximately 15 degrees from vertical on average. length: approximately 3.0 mm on average. diameter: approximately 6.0 mm on average. texture: pubescent. color: Greyed-Green Group 196A.

*Reproductive organs Androecium*.—Stamen quantity per flower: approximately 75 on average. filament length: approximately 1.4 mm on average. filament color. White Group N155B. anther shape: fused. anther length: approximately 1.5 mm on average. anther color. White Group 155A. pollen amount: moderate. pollen color. Yellow Group 11B.

*Gynoecium*.—pistil quantity per flower: 1, fused with 5 protruding stigma from the top. pistil length: approximately 2.3 cm on average. stigma shape: peltate. stigma color: White Group 155A. style length: approximately 1.8 cm on average. style color: White Group NN155B. ovary diameter: approximately 4.5 mm on average. ovary color: Yellow-Green Group 145B.

Development:

*Blossoming*.—Summer through early fall.

*Seed and fruit production*.—Neither seed nor fruit production have been observed.

*Resistance to disease and pests*.—Neither resistance nor susceptibility to normal diseases and pests of hibiscus have been observed.

The new 'Minsycbb2b' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of hibiscus plant named 'Minsycbb2b' characterized by the following combination of characteristics:

(a) forms white and light blue-colored inflorescences, (b) displays medium green-colored foliage, and (c) exhibits a tall, semi-upright growth habit;

substantially as herein shown and described.

* * * * *